(12) United States Patent
Gloth et al.

(10) Patent No.: US 10,702,172 B2
(45) Date of Patent: *Jul. 7, 2020

(54) BLOOD PRESSURE CUFF WITH TAPERED BLADDER

(71) Applicant: ST. LUKE MEDICAL, INC., Clarksville, MD (US)

(72) Inventors: Sean T. Gloth, Clarksville, MD (US); Christopher Gloth, Clarksville, MD (US)

(73) Assignee: ST. LUKE MEDICAL, INC., Clarksville, MD (US)

( * ) Notice: Subject to any disclaimer, the term of this patent is extended or adjusted under 35 U.S.C. 154(b) by 203 days.

This patent is subject to a terminal disclaimer.

(21) Appl. No.: 15/511,677

(22) PCT Filed: Sep. 16, 2015

(86) PCT No.: PCT/US2015/050489
§ 371 (c)(1),
(2) Date: Mar. 16, 2017

(87) PCT Pub. No.: WO2016/044459
PCT Pub. Date: Mar. 24, 2016

(65) Prior Publication Data
US 2017/0296073 A1 Oct. 19, 2017

Related U.S. Application Data

(60) Provisional application No. 62/050,956, filed on Sep. 16, 2014.

(51) Int. Cl.
A61B 5/022 (2006.01)
A61B 5/025 (2006.01)
(Continued)

(52) U.S. Cl.
CPC .......... *A61B 5/02233* (2013.01); *A61B 5/022* (2013.01); *A61B 5/025* (2013.01); *A61B 7/045* (2013.01); *A61B 17/135* (2013.01)

(58) Field of Classification Search
CPC ..... A61B 5/02233; A61B 5/022; A61B 5/025; A61B 7/045; A61B 17/135
See application file for complete search history.

(56) References Cited

U.S. PATENT DOCUMENTS 3,504,675 A * 4/1970 Bishop, Jr. .......... A61B 17/1322
606/202
4,458,690 A * 7/1984 O'Connor .......... A61B 5/02208
24/21

(Continued)

*Primary Examiner* — Matthew Kremer
*Assistant Examiner* — Avery M Foley
(74) *Attorney, Agent, or Firm* — Pepper Hamilton LLP

(57) ABSTRACT

A blood pressure cuff may comprise an alignment component, a sleeve, and a tapered inflatable bladder disposed within the sleeve. The tapered inflatable bladder may have a width that increases as the distance from the alignment component increases, and the tapered inflatable bladder and the alignment component may be configured to position the blood pressure cuff around a limb having a blood vessel and a circumference, such that at a position coincident with the blood vessel, the width of the tapered inflatable bladder is about 40% of the circumference of the limb. A method of using such a blood pressure cuff may comprise placing the alignment component at the position coincident with the blood vessel of the limb, wrapping the cuff around the limb such that the width of the tapered inflatable bladder overlaying the blood vessel is about 40% of the circumference of the limb, and inflating the bladder.

19 Claims, 9 Drawing Sheets

(51) Int. Cl.
*A61B 17/135* (2006.01)
*A61B 7/04* (2006.01)

(56) References Cited

U.S. PATENT DOCUMENTS

| | | | | |
|---|---|---|---|---|
| 4,901,732 | A * | 2/1990 | Williams | A61B 5/02233 |
| | | | | 600/499 |
| 9,743,847 | B2 * | 8/2017 | Gloth | A61B 5/02233 |
| 2005/0182331 | A1 * | 8/2005 | Millay | A61B 5/02233 |
| | | | | 600/499 |
| 2006/0293600 | A1 * | 12/2006 | Wawro | A61B 5/02141 |
| | | | | 600/490 |
| 2007/0135720 | A1 * | 6/2007 | Vinocur | A61B 5/02233 |
| | | | | 600/499 |
| 2009/0043215 | A1 * | 2/2009 | Grassl | A61B 5/02233 |
| | | | | 600/499 |
| 2012/0130419 | A1 * | 5/2012 | Leschinsky | A61B 5/02208 |
| | | | | 606/202 |

* cited by examiner

BLOOD PRESSURE CUFF WITH TAPERED BLADDER

CROSS-REFERENCE TO RELATED APPLICATIONS

This application claims priority to and benefit of U.S. Provisional Application Ser. No. 62/050,956 filed Sep. 16, 2014, entitled "Blood Pressure Cuff with Tapered Bladder," the disclosure of which is incorporated herein by reference in its entirety.

BACKGROUND

Blood pressure is typically measured using a sphygmomanometer, otherwise known as a blood pressure cuff. A blood pressure cuff typically includes a sleeve with an inflatable bladder attached to a manometer. The sleeve is wrapped around a subject's limb, and the bladder is then inflated to restrict blood flow through a blood vessel within the limb. The manometer is used to read the pressure at which the blood flow first resumes and the pressure at which the blood flow becomes unimpeded.

SUMMARY

In some embodiments, a blood pressure cuff may comprise an alignment component, a sleeve, and a tapered inflatable bladder disposed within the sleeve. In some embodiments, the tapered inflatable bladder may have a width that increases as the distance from the alignment component increases, and the tapered inflatable bladder and the alignment component may be configured to position the blood pressure cuff around a limb having a blood vessel and a circumference, such that at a position coincident with the blood vessel, the width of the tapered inflatable bladder is about 40% of the circumference of the limb.

In some embodiments, a method of using a blood pressure cuff may comprise providing a blood pressure cuff having an alignment component, a sleeve, and a tapered bladder disposed around the sleeve, wherein the tapered inflatable bladder may have a width that increases as the distance from the alignment component increases, and the tapered inflatable bladder and the alignment component may be configured to position the blood pressure cuff around a limb having a blood vessel and a circumference, such that at a position coincident with the blood vessel, the width of the tapered inflatable bladder is about 40% of the circumference of the limb. The method of using a blood pressure cuff may further comprise placing the alignment component at the position coincident with the blood vessel of the limb, wrapping the cuff around the limb, thereby causing the width of the tapered inflatable bladder to overlay a portion of the blood vessel such that the width of the tapered inflatable bladder is about 40% of the circumference of the limb, and inflating the bladder.

DETAILED DESCRIPTION

Figure 1:
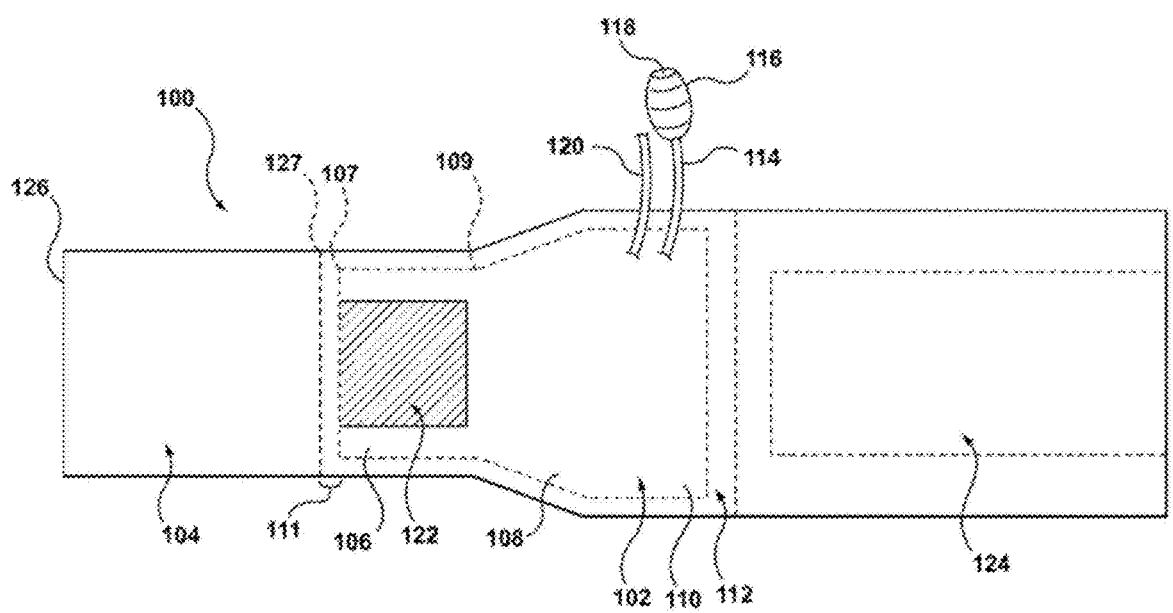
FIG. 1 schematically illustrates a blood pressure cuff with a linearly tapered inflatable bladder and an alignment component, in accordance with the present disclosure.

A subject's blood pressure is most commonly measured using a sphygmomanometer or blood pressure cuff. A blood pressure cuff typically comprises an inflatable bladder housed within a sleeve and connected to a manometer. The cuff is typically wrapped around the subject's limb, or a portion thereof, and the bladder is inflated to restrict blood flow through a blood vessel within the limb. The manometer is used to read the pressure at which the blood flow first resumes (known as the systolic blood pressure, or SBP), and the pressure at which the blood flow becomes unimpeded (known as the diastolic blood pressure, or DBP). The sounds corresponding with the SBP and DBP, known as Korotkoff sounds, may be identified manually, using a stethoscope, or may be identified automatically, using an electronic calculation.

A typical blood pressure cuff is sized for a range of arm circumferences, yet contains an inflatable bladder of a fixed width. However, the SBP and DBP read by the manometer vary as the ratio of the inflatable bladder width to the limb circumference varies. As a result, the blood pressure of a subject whose limb circumference does not fall at the center of the range corresponding to a given cuff size will be measured inaccurately. In an attempt to mitigate this problem, the American Heart Association (AHA) has recommended using seven different cuff sizes, corresponding to seven different arm circumference ranges, for subjects ranging in size from pediatric to large adult. However, because each of the seven cuff sizes contains a fixed-width inflatable bladder, using even the recommended cuff can result in an error up to plus or minus 5% in SBP and DBP readings. Furthermore, because following the AHA recommendation requires measuring the subject's limb circumference before choosing the appropriate cuff size, many practitioners ignore the recommendation and use a standard cuff size with a 12 cm bladder width for almost all blood pressure measurements. This misuse can result in even larger errors in SBP and DBP readings. In some tests, errors have been on the order of 5-10 mmHg for both the SBP and the DBP.

Such blood pressure measurement errors can lead to costly misdiagnoses, especially for subjects whose blood pressures are near the cutoff levels for prescribing treatment for hypertension. Because of such cutoff levels, erroneously high blood pressure measurements may cause subjects to be prescribed hypertension medication when those subjects do not actually need such medication. Such misdiagnosis results in increased healthcare costs, and unnecessarily medicated subjects. Similarly, erroneously low blood pressure measurements may cause subjects who need hypertension medication not to receive it, thereby resulting in costly and dangerous health complications associated with untreated hypertension.

It has been suggested that the ratio of the width of the inflatable bladder covering the blood vessel of the subject's limb to the circumference of the limb should be about 40% in order for the bladder to properly occlude the blood vessel once inflated. It has also been suggested that the inflatable bladder should encircle at least about 80% of the limb, and less than 100% of the limb, in order to provide accurate blood pressure measurements. Therefore, the need exists for a blood pressure cuff that meets these accuracy requirements while accommodating a range of subjects with a range of limb circumferences.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "bladder" is a reference to one or more bladders and equivalents thereof known to those skilled in the art, and so forth.

As used herein, the terms "about" and "approximately" mean plus or minus 10% of the numerical value of the number with which it is being used. Therefore, about 40% means in the range of 30%-50%.

The terms "animal," "patient," and "subject" as used herein include, but are not limited to, humans and non-human vertebrates such as wild, domestic and farm animals. In some embodiments, the terms "animal," "patient," and "subject" may refer to humans.

The terms "sphygmomanometer" and "blood pressure cuff" are used interchangeably throughout the present disclosure, and are understood by those of ordinary skill in the art to be interchangeable terms.

As used herein, the term "tapered inflatable bladder" may refer to variety of bladder configurations, including a bladder having a tapered configuration, or a standard bladder disposed within a sleeve or other housing having a tapered configuration, such that the sleeve confines the expansion of the bladder, limiting it to a tapered configuration when inflated.

Embodiments of the blood pressure cuff described herein may be sized for and applied to any limb or portion thereof. In some embodiments, the blood pressure cuff may be applied to a subject's upper arm, and the placement of an alignment component may coincide with the subject's brachial artery. In some embodiments, the blood pressure cuff may be applied to a subject's forearm, and the placement of the alignment component may coincide with the subject's ulnar or radial artery. In some embodiments, the blood pressure cuff may be applied to a subject's thigh or upper leg, and the placement of the alignment component may coincide with the subject's femoral artery or popliteal artery. In some embodiments, the blood pressure cuff may be applied to a subject's calf or lower leg, and the placement of the alignment component may coincide with the subject's fibular or tibial artery.

In some embodiments, a blood pressure cuff may comprise an alignment component, a sleeve, and a tapered inflatable bladder disposed within the sleeve. The tapered inflatable bladder may have a width that increases as the distance from the alignment component increases, and the tapered inflatable bladder and the alignment component may be configured to position the blood pressure cuff around a limb having a blood vessel and a circumference, such that at a position coincident with the blood vessel, the width of the tapered inflatable bladder is a particular percentage of the circumference of the limb. In some embodiments, the particular percentage may be in the range from about 30% to about 50%. The particular percentage may be, for example, 30%, 31%, 32%, 33%, 34%, 35%, 36%, 37%, 38%, 39%, 40%, 41%, 42%, 43%, 44%, 45%, 46%, 47%, 48%, 49%, 50%, or any value between any of these percentages, including endpoints. In some embodiments, the blood pressure cuff may further comprise a rectangular section having a first end and a second end opposite the first end.

In some embodiments, the alignment component may comprise an edge. In such embodiments, the edge may be placed in a position coincident with the blood vessel of the limb of interest. In some embodiments, the alignment component may comprise one or more discrete marks, such as lines, on the sleeve of the blood pressure cuff. In such embodiments, the discrete marks may be aligned with the blood vessel of the limb of interest. In some embodiments, the discrete marks may be on any surface of the sleeve. In some embodiments, the discrete marks may be on the surface of the sleeve that is opposite the surface touching the limb of the subject. The alignment component may comprise any material such as, for example, fabric, nylon, plastic, metal, or any other similar material. The alignment component may be of any shape. In some embodiments, the alignment component may be wider than the sleeve of the blood pressure cuff. In some embodiments, the alignment component may be narrower than the sleeve of the blood pressure cuff.

In some embodiments, the sleeve of the blood pressure cuff may generally mimic the shape of the tapered inflatable bladder. In some embodiments, the shape of the sleeve may be any shape larger than the inflatable bladder. In some embodiments, the sleeve may use seams, fasteners, or other fixtures to ensure that the tapered inflatable bladder does not shift substantially within the sleeve. The sleeve may comprise any fabric or other sufficiently flexible material. In some embodiments, the sleeve may comprise nylon. In some embodiments, the sleeve of the blood pressure cuff may further comprise fasteners disposed on one or more of the first side of the sleeve and the second side of the sleeve, wherein the first side opposes the second side. In some embodiments, the fasteners may be used to affix a first portion of the blood pressure cuff to a second portion of the blood pressure cuff, such that the cuff maintains a substantially fixed position once the fasteners are employed. In some embodiments, the fasteners may be used to affix the blood pressure cuff to the subject's limb. In some embodiments, the fasteners may comprise one or more hook and loop closures.

In some embodiments, the inflatable bladder may itself have a tapered configuration. In some embodiments, the "tapered inflatable bladder" may be formed by disposing a standard bladder within a sleeve or other housing having a tapered configuration, such that the sleeve confines the expansion of the bladder, limiting it to a tapered configuration when inflated. In some embodiments, the tapered inflatable bladder may comprise polyvinyl chloride (PVC), rubber, a polymer, or any other material that is generally impermeable to air. In some embodiments, the tapered inflatable bladder may comprise two layers, which may form a pocket for holding the air. In some embodiments, the tapered inflatable bladder may comprise a linear taper. In some embodiments, the tapered inflatable bladder may comprise a curved taper. In some embodiments, the tapered inflatable bladder may comprise a logarithmic taper. In some embodiments, the tapered inflatable bladder may be inflated manually. In some embodiments, the tapered inflatable bladder may be inflated automatically.

In some embodiments, the blood pressure cuff may further comprise one or more tubes configured to transport air to and from the tapered inflatable bladder. The one or more tubes configured to transport air may be affixed to any portion and any location of the tapered inflatable bladder. In some embodiments, the distal end of the one or more tubes configured to transport air may be connected to an air pump. In some embodiments, the air pump may comprise a squeeze ball. In some embodiments, the air pump may comprise an automatic pumping device.

In some embodiments, the blood pressure cuff may further comprise one or more tubes configured to transmit sound from the tapered inflatable bladder. The one or more tubes configured to transmit sound may be affixed to any portion and any location of the tapered inflatable bladder.

In some embodiments, the blood pressure cuff may further comprise at least one sensor. In some embodiments, the alignment component may comprise the sensor. In some embodiments, the sleeve may comprise the sensor. In some embodiments, the sensor may be configured to detect pressure, such as, for example, the pressure of the air within any component of the blood pressure cuff. In some embodiments, the sensor may be configured to detect sound, such as, for example, the Korotkoff sounds associated with the SBP and DBP of the subject.

In some embodiments, the blood pressure cuff may further comprise a ring disposed at an end of the sleeve. The ring may be used to wrap the blood pressure cuff around the limb of the subject, wherein a portion of the sleeve is extended through the ring, and subsequently wrapped back toward the direction of the portion of the sleeve. In some embodiments, the ring may comprise a plastic, a metal, or a fabric. In some embodiments, the ring may be a D-shaped ring.

In some embodiments, a method of using a blood pressure cuff may comprise providing a blood pressure cuff having an alignment component, a sleeve, and a tapered bladder disposed around the sleeve, wherein the tapered inflatable bladder may have a width that increases as the distance from the alignment component increases, and the tapered inflatable bladder and the alignment component may be configured to position the blood pressure cuff around a limb having a blood vessel and a circumference, such that at a position coincident with the blood vessel, the width of the tapered inflatable bladder is about 40% of the circumference of the limb. The method of using a blood pressure cuff may further comprise placing the alignment component at the position coincident with the blood vessel of the limb, wrapping the cuff around the limb, thereby causing the width of the tapered inflatable bladder to overlay a portion of the blood vessel such that the width of the tapered inflatable bladder is about 40% of the circumference of the limb, and inflating the bladder.

FIG. 1 illustrates a schematic view of a blood pressure cuff 100 with a tapered inflatable bladder 102 and an alignment component 104. The tapered inflatable bladder 102 may include a narrow rectangular section 106, a linearly tapered section 108, and a wide rectangular section 110. The tapered inflatable bladder 102 is shown in FIG. 1 in dashed lines because it is housed within a sleeve 112. A first end of one or more tubes 114 may each be connected at a first end to an internal pocket of the inflatable bladder 102, and a second end of the one or more tubes 114 may be connected to a squeeze ball. An opening 118 in the squeeze ball 116 allows atmospheric air to enter the squeeze ball 116. When the squeeze ball 116 is compressed, air is transferred through the one or more tubes 114 to the tapered inflatable bladder 102, causing it to inflate. A second set of one or more tubes 120 may each have a first end connected to the internal pocket of the tapered inflatable bladder 102 and a second end (not shown) connected to a manometer (not shown). In the embodiment of FIG. 1, hook and loop sections 122 and 124 on opposing sides of the cuff 100 are used to secure the cuff 100 around a subject's limb.

Figure 2:
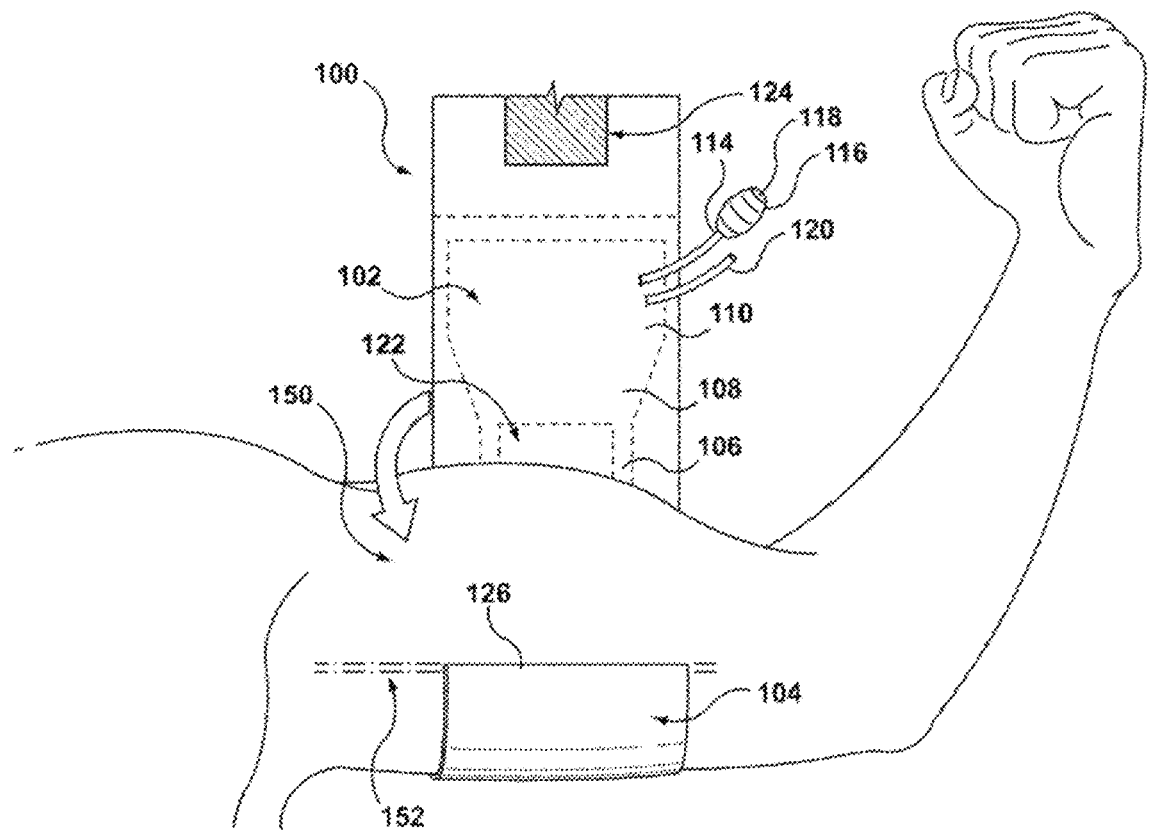
FIG. 2 schematically illustrates a method of aligning a blood pressure cuff on a subject's limb such that the cuff's tapered inflatable bladder contacts a blood vessel within the limb at an appropriate positions for an accurate blood pressure reading, in accordance with the present disclosure.

FIG. 2 schematically illustrates a method of aligning a blood pressure cuff 100 with a subject's limb 150. As shown in FIG. 2, an edge 126 of the alignment component 104 may be placed tangentially to a blood vessel 152 within the subject's limb. The cuff 100 may be wrapped around the limb 150 such that tapered inflatable bladder 102 intersects the blood vessel 152, and the cuff 100 may then be fixed into position by attaching hook and loop sections 122 and 124 to each other. It is important that the method of aligning the cuff 100 is easy so that users properly align it such that the proper width of the tapered inflatable bladder 102 is aligned with the blood vessel 152.

The alignment component 104 may be sized according to the range of limb circumferences for which the cuff 100 is intended. The length of the alignment component 104 that wraps around subject's limb 150 is such that the narrow rectangular section 106 of the tapered inflatable bladder 102 intersects the blood vessel 152 if the subject's limb circumference is equal to the minimum value supported by the particular size of cuff 100. Similarly, the alignment component 104 ensures that the wide rectangular section 110 intersects the blood vessel 152 if the subject's limb circumference is equal to the maximum value supported by the cuff size, and that the appropriate portion of the linearly tapered section 108 intersects the blood vessel if the subject's limb circumference falls between the limits supported by the size of cuff the 100. This design ensures that the ratio of the width of the tapered inflatable bladder 102 (at the point where it intersects the blood vessel 152) to the limb circumference is maintained at the desired width of bladder to limb circumference ratios for any limb circumference failing within the range supported by the size of the cuff 100. Additionally, the lengths of the alignment component 104 and the tapered inflatable bladder 102 are such that, for an arm circumference falling within the bounds specified by the size of the cuff 100, the tapered inflatable bladder 102 encircles the subject's limb 150 without overlapping onto itself.

Accordingly, as can be seen in the charts provided below, the length of the alignment component 104 and the length of the narrow rectangular section 106 of the tapered inflatable bladder 102 add up to nearly the minimum limb circumference for the cuff 100. The total may not equal the minimum limb circumference because there may be a distance or gap 111 from a second end 127 of the alignment component 104 to an edge 107 of the narrow rectangular section 106 of the tapered inflatable bladder 102 of approximately 2 cm. Accordingly, the length from the edge 126 of the alignment component 104 to a transition 109 from the narrow rectangular section 106 of the tapered inflatable bladder 102 to the tapered section 108 of the tapered inflatable bladder 102 is approximately equal to the minimum limb circumference for the cuff. Those skilled in the art would recognize that variations in the length of the alignment component 104, the narrow rectangular section 106, and the gap 111 may be made provided that the total length from the edge 126 of the alignment component 104 to the transition 109 is approximately the minimum circumference for the cuff. The table below provides exemplary sizes of parts of the cuff 100 for particular ranges of limb circumferences. The reference numerals used in the chart refer the FIG. 1. but the chart applies equally to the embodiment of FIG. 3 as described below. All numbers provided within the table are in centimeters.

Figure 3:
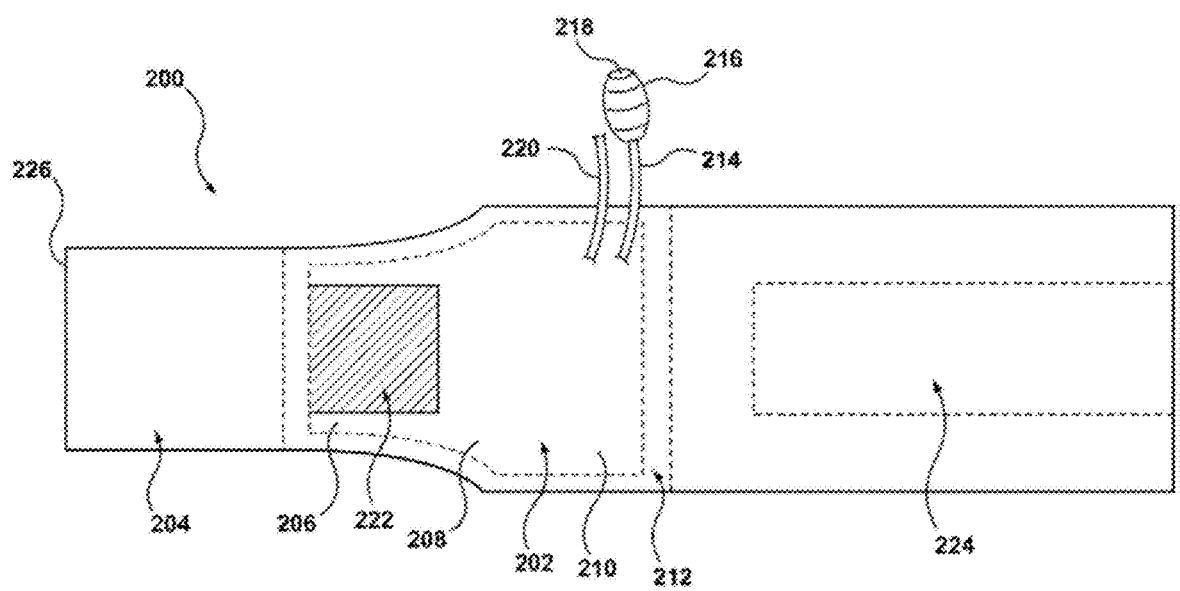
FIG. 3 schematically illustrates a blood pressure cuff with a curvedly tapered inflatable bladder and an alignment component, in accordance with the present disclosure.
Figure 7:
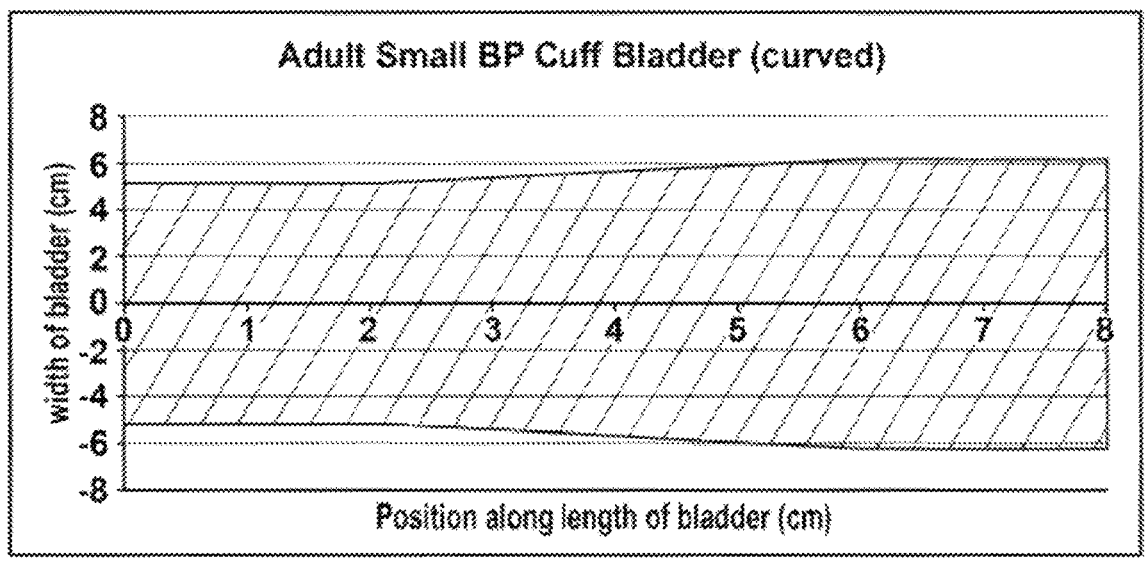
FIG. 7 graphically illustrates the width of a bladder in relation to a lengthwise distance from an edge of a curvedly tapered inflatable bladder for a small blood pressure cuff, in accordance with the present disclosure.
Figure 8:
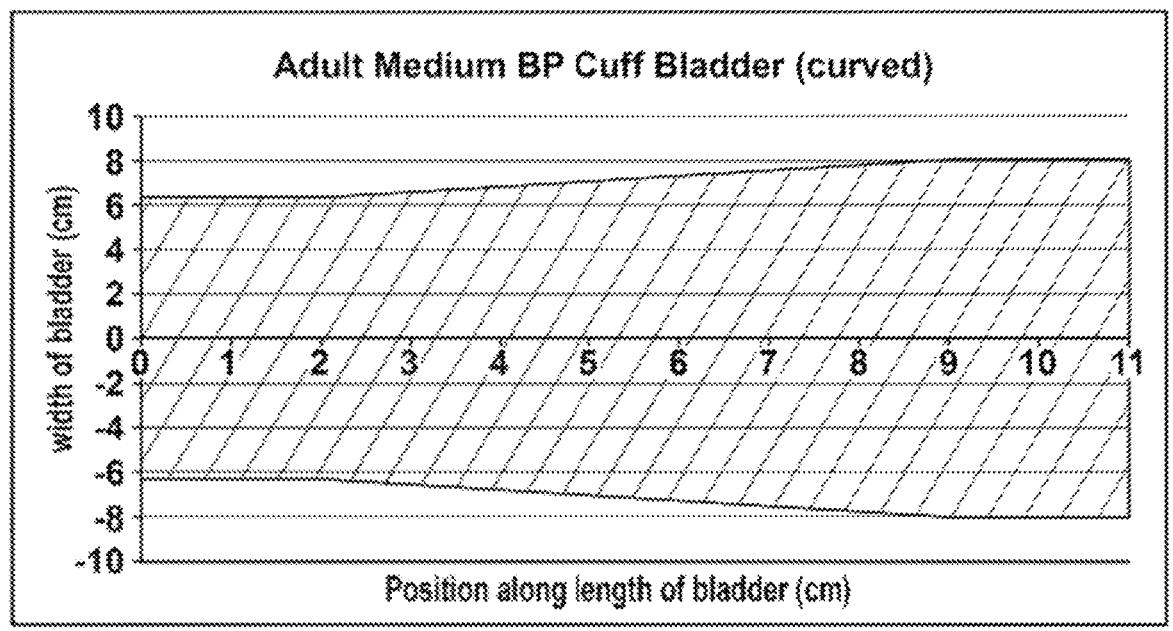
FIG. 8 graphically illustrates the width of a bladder in relation to a lengthwise distance from an edge of a curvedly tapered inflatable bladder for a medium blood pressure cuff, in accordance with the present disclosure.
Figure 9:
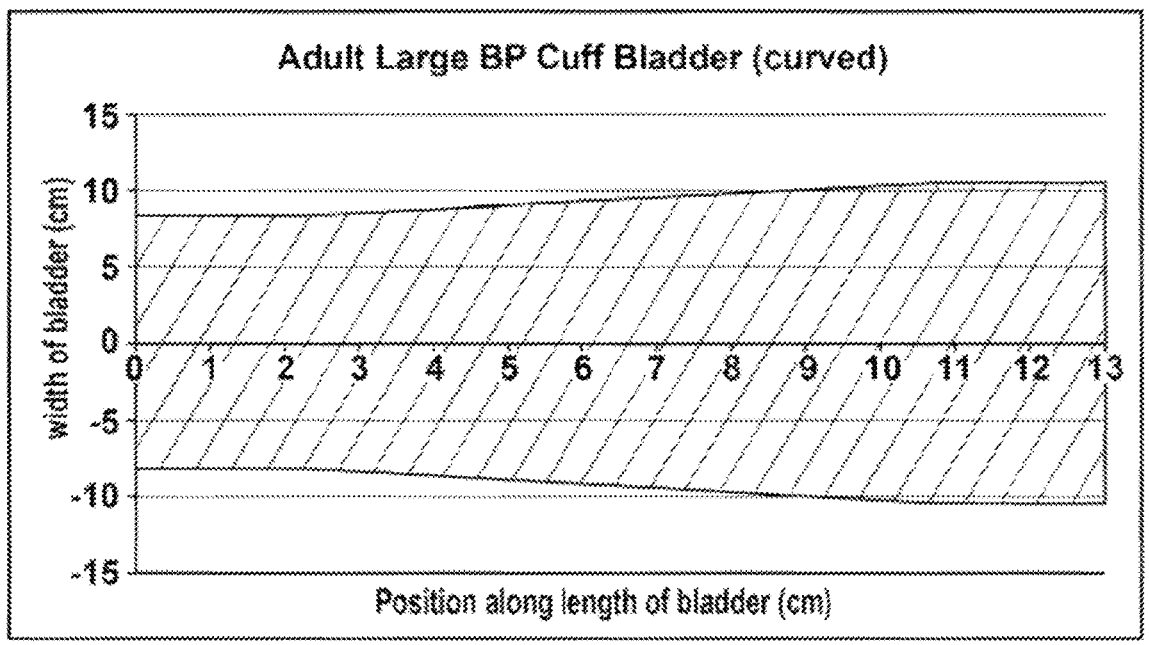
FIG. 9 graphically illustrates the width of a bladder in relation to a lengthwise distance from an edge of a curvedly tapered inflatable bladder for a large blood pressure cuff, in accordance with the present disclosure.

FIG. 3 illustrates a schematic view of another embodiment of a blood pressure cuff 200, which also contains a tapered inflatable bladder 202 and an alignment component 204. The cuff 200 of this embodiment is similar to the cuff 100 except that the tapered inflatable bladder 202 includes a curved tapered section 208 between a narrow rectangular section 206 and a wide rectangular section 210. It has been found that a suitable curve is defined by the following formula: $W=(C-LOG(C))/2$; wherein C is approximately equal to the circumference of the subject's limb and W is equal to the width of the tapered section for a particular circumference. Accordingly, whereas the chart above with the linear tapered section used the above formula for the width of the tapered inflatable bladder at the narrow rectangular section and the wide rectangular section, the chart below uses this formula for each width. FIGS. 7-9 are graphs showing the bladder in accordance with the formula above for small, medium, and large blood pressure cuffs, respectively. Otherwise, the cuff 200 is similar to the previously described cuff 100. The tapered inflatable bladder 202 is housed within a sleeve 212 and may be inflated or deflated via one or more tube 214 and a squeeze ball 216. A second set of one or more tubes 220 may have a first end connected to the internal pocket of the tapered inflatable bladder 202 and a second end (not shown) connected to a manometer (not shown). The shapes and materials of the tapered inflatable bladder 202, the alignment 204, the sleeve 212, and opposing hook and loop sections 222 and 224 are as previously described. The cuff 200 is aligned with the subject's limb in the same manner as illustrated in FIG. 2 and discussed above.

Although specific embodiments of the linear taper and curved taper have been presented above, those skilled in the

| Cuff Size | Limb Circ. Range | Alignment Comp. 104 Length | Narr. Rect. 106 Length | Narr. Rect. 106 Width | Taper 108 Length | Wide Rect. 110 Length | Wide Rect. 110 Width |
|---|---|---|---|---|---|---|---|
| Small | 22-26 | 19 | 2 | 10.33 | 4 | 2 | 12.29 |
| Medium | 27-34 | 24 | 2 | 12.78 | 7 | 2 | 16.23 |
| Large | 35-44 | 32 | 2 | 16.73 | 9 | 2 | 21.18 |

Figure 4:
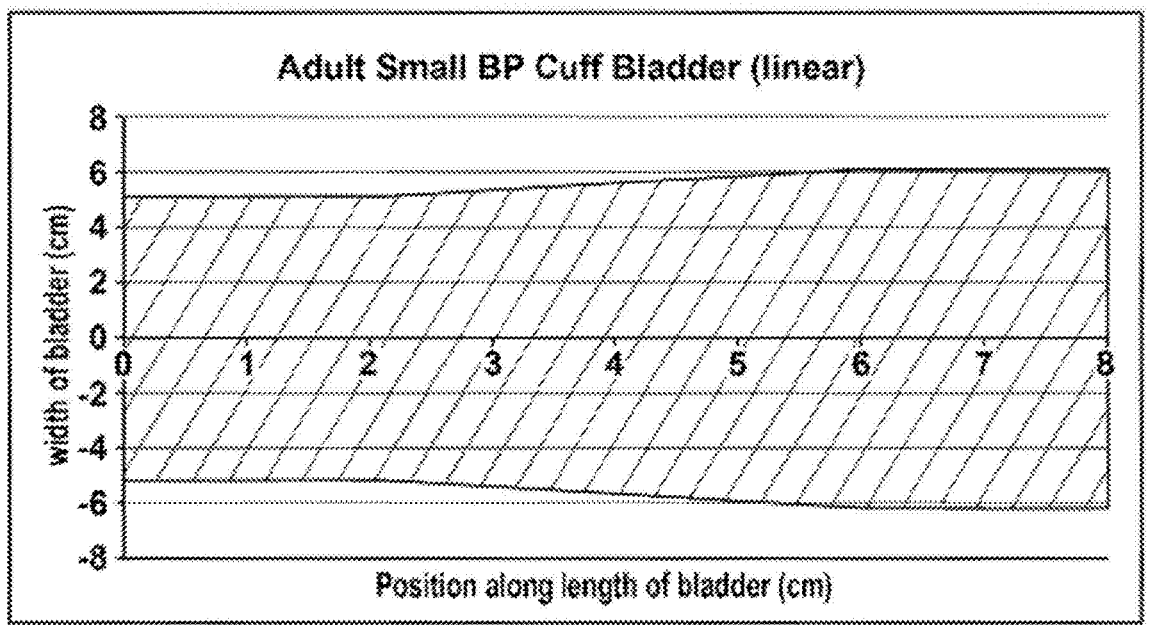
FIG. 4 graphically illustrates the width of a bladder in relation to a lengthwise distance from an edge of a linearly tapered inflatable bladder for a small blood pressure cuff, in accordance with the present disclosure.
Figure 5:
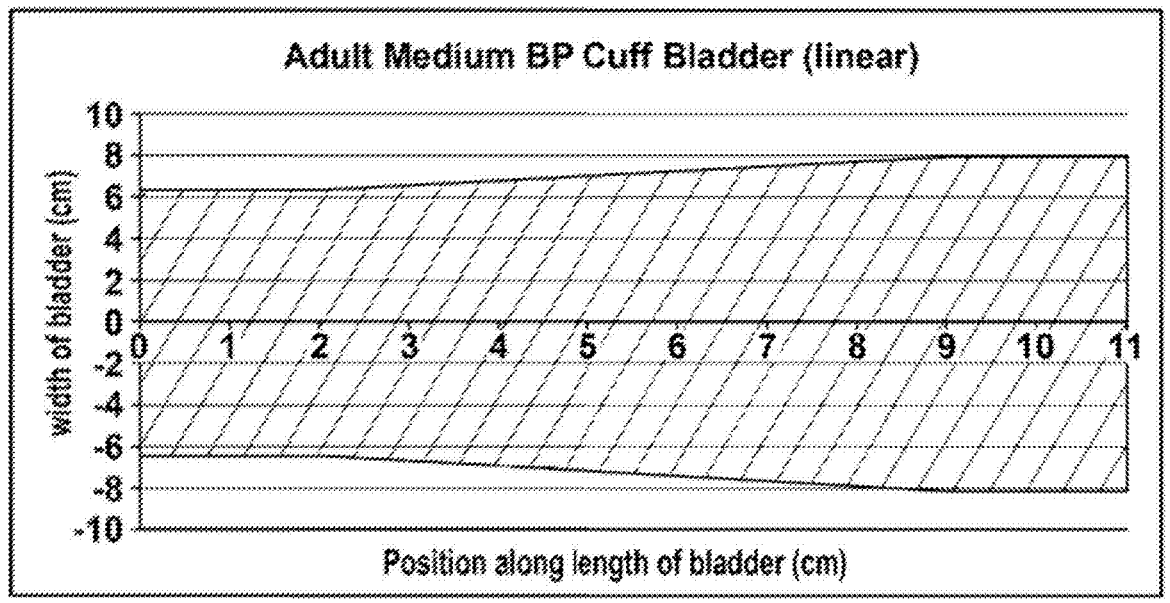
FIG. 5 graphically illustrates the width of a bladder in relation to a lengthwise distance from an edge of a linearly tapered inflatable bladder for a medium blood pressure cuff, in accordance with the present disclosure.
Figure 6:
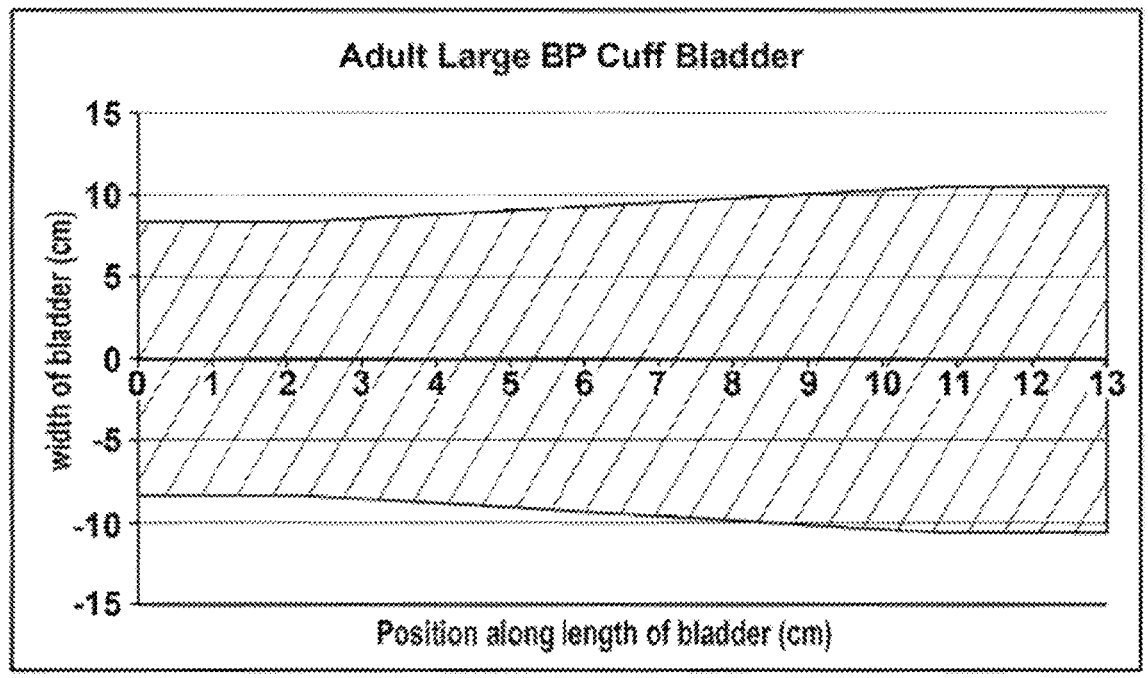
FIG. 6 graphically illustrates the width of a bladder in relation to a lengthwise distance from an edge of a linearly tapered inflatable bladder for a large blood pressure cuff, in accordance with the present disclosure.

In the chart, above, the tapered inflatable bladder is linearly tapered. Thus, the width of the bladder along the taper length can be calculated by the commonly known formula for a line: $Y=m*X+b$, wherein m is equal to the slope and b is equal to the Y-axis intercept. In order to calculate the formula for the line of the tapered section, the bladder parameters may be laid out on a graph. Two points on the line can be determined by ½ the width of the bladder in the narrow section as the Y-axis at 2 cm along the X-axis and ½ the width of the wide section of the bladder as the Y-axis at 6 cm along the X-axis. One half of the width is used such that half of the bladder is above the X-axis and half of the bladder is below the X-axis. Solving the equation results in the line of the tapered section of the bladder of the small cuff identified above being defined as $Y=0.245*X+4.675$. FIGS. 4-6 show graphs of the bladder sections for small, medium, and large cuffs, respectively, with the dimensions as noted above. Further, the width at the narrow rectangular section 106 and the width of the wide rectangular section 110 are each approximately calculated according to the formula: $W=(C-LOG(C))/2$; wherein C is approximately equal to the circumference of the subject's limb and W is equal to the width of the tapered section for a particular circumference.

art would recognize that other linear tapers or curved tapers may be used. For example, in a linear taper embodiment, the ratio of the width of the tapered inflatable bladder covering the blood vessel to the subject's limb circumference may be approximately 47%. The design of the taper of the bladder may be modified to accommodate any desired ratio. For example, and not by way of limitation, a bladder of a blood pressure cuff may be designed to accommodate a 40% ratio using the following cuff and bladder dimensions, expressed in centimeters.

| Cuff Size | Limb Circ. | Alignment Comp. Length | Distance from Narrow Bladder Edge | Bladder Width |
|---|---|---|---|---|
| Small | 22 | 19 | 0 | 8.8 |
| Small | 22 | 19 | 1 | 8.8 |
| Small | 22 | 19 | 2 | 8.8 |
| Small | 23 | 19 | 3 | 9.2 |
| Small | 24 | 19 | 4 | 9.6 |
| Small | 25 | 19 | 5 | 10 |
| Small | 26 | 19 | 6 | 10.4 |
| Small | 26 | 19 | 7 | 10.4 |
| Small | 26 | 19 | 8 | 10.4 |

-continued

| Cuff Size | Limb Circ. | Alignment Comp. Length | Distance from Narrow Bladder Edge | Bladder Width |
|---|---|---|---|---|
| Medium | 27 | 24 | 0 | 10.8 |
| Medium | 27 | 24 | 1 | 10.8 |
| Medium | 27 | 24 | 2 | 10.8 |
| Medium | 28 | 24 | 3 | 11.2 |
| Medium | 29 | 24 | 4 | 11.6 |
| Medium | 30 | 24 | 5 | 12.0 |
| Medium | 31 | 24 | 6 | 12.4 |
| Medium | 32 | 24 | 7 | 12.8 |
| Medium | 33 | 24 | 8 | 13.2 |
| Medium | 34 | 24 | 9 | 13.6 |
| Medium | 34 | 24 | 10 | 13.6 |
| Medium | 34 | 24 | 11 | 13.6 |
| Large | 35 | 32 | 0 | 14.0 |
| Large | 35 | 32 | 1 | 14.0 |
| Large | 35 | 32 | 2 | 14.0 |
| Large | 36 | 32 | 3 | 14.4 |
| Large | 37 | 32 | 4 | 14.8 |
| Large | 38 | 32 | 5 | 15.2 |
| Large | 39 | 32 | 6 | 15.6 |
| Large | 40 | 32 | 7 | 16.0 |
| Large | 41 | 32 | 8 | 16.4 |
| Large | 42 | 32 | 9 | 16.8 |
| Large | 43 | 32 | 10 | 17.2 |
| Large | 44 | 32 | 11 | 17.6 |
| Large | 44 | 32 | 12 | 17.6 |
| Large | 44 | 32 | 13 | 17.6 |

Those skilled in the art would recognize that variations in the desired ratio of tapered inflatable bladder width to limb circumference, length of narrow rectangular section of the bladder, and length of the alignment component may be made such that the desired width of the tapered inflatable bladder corresponds to each limb circumference with the alignment method described above.

While the present disclosure has been illustrated by the description of exemplary embodiments thereof, and while the embodiments have been described in certain detail, it is not the intention of the Applicants to restrict or in any way limit the scope of the appended claims to such detail. Additional advantages and modifications will readily appear to those skilled in the art. Therefore, the disclosure in its broader aspects is not limited to any of the specific details, representative devices and methods, and/or illustrative examples shown and described. Accordingly, departures may be made from such details without departing from the spirit or scope of the Applicants' general inventive concept.

What is claimed is:

1. A blood pressure cuff comprising:
an alignment component having a front straight edge;
a sleeve; and
a tapered inflatable bladder disposed within the sleeve, wherein the tapered inflatable bladder has a width that increases as the distance from the front straight edge increases, and wherein the tapered inflatable bladder and the alignment component are configured to position the blood pressure cuff around a limb having a blood vessel and a circumference such that at a position coincident with the blood vessel, the width of the tapered inflatable bladder is about 40% of the circumference of the limb for any circumference within a range of circumferences;
wherein the alignment component has a length between the front straight edge and the tapered inflatable bladder;
wherein the tapered inflatable bladder does not extend into the alignment component; and
wherein the front straight edge of the alignment component is configured to be placed at the position coincident with the blood vessel.

2. The blood pressure cuff of claim 1, further comprising a rectangular section having a first end and a second end opposite the first end.

3. The blood pressure cuff of claim 2, wherein a length from an end of the alignment component opposite the edge to the second end of the rectangular section is from about 19 cm to about 35 cm.

4. The blood pressure cuff of claim 2, wherein the circumference of the limb is from about 27 cm to about 34 cm, and a length from an end of the alignment component opposite the front straight edge to the second end of the rectangular section is about 27 cm.

5. The blood pressure cuff of claim 1, wherein the tapered inflatable bladder is logarithmically tapered.

6. The blood pressure cuff of claim 1, wherein the tapered inflatable bladder is curvedly tapered.

7. The blood pressure cuff of claim 1, wherein the tapered inflatable bladder is linearly tapered.

8. The blood pressure cuff of claim 1, further comprising at least one tube configured to transport air to and from the tapered inflatable bladder.

9. The blood pressure cuff of claim 1, further comprising at least one tube configured to transmit sound from the tapered inflatable bladder.

10. The blood pressure cuff of claim 1, further comprising at least one sensor configured to detect sound.

11. The blood pressure cuff of claim 1, further comprising at least one sensor configured to detect pressure.

12. The blood pressure cuff of claim 1, further comprising a ring disposed at an end of the sleeve.

13. The blood pressure cuff of claim 1, wherein the range of circumferences is a continuous range of circumferences.

14. A method of using a blood pressure cuff, the method comprising:
providing a blood pressure cuff comprising:
an alignment component having a front straight edge;
a sleeve; and
a tapered inflatable bladder disposed within the sleeve, wherein the tapered inflatable bladder has a width that increases as the distance from the front straight edge increases, and wherein the tapered inflatable bladder and the alignment component are configured to position the blood pressure cuff around a limb having a blood vessel and a circumference such that at a position coincident with the blood vessel, the width of the tapered inflatable bladder is about 40% of the circumference of the limb for any circumference within a range of circumferences;
wherein the alignment component has a length between the front straight edge and the tapered inflatable bladder, and wherein the tapered inflatable bladder does not extend into the alignment component;
placing the front straight edge of the alignment component at the position coincident with the blood vessel of the limb;
wrapping the blood pressure cuff around the limb, thereby causing the width of the tapered inflatable bladder to overlay a portion of the blood vessel such that the width of the tapered inflatable bladder is about 40% of the circumference of the limb; and
inflating the bladder.

15. The method of claim 14, wherein the blood pressure cuff further comprises a rectangular section having a first end and a second end opposite the first end.

16. The method of claim 14, wherein the sleeve of the blood pressure cuff further comprises one or more hook and loop sections disposed on each of a first side of the sleeve and a second side of the sleeve, wherein the first side opposes the second side.

17. The method of claim 16, further comprising attaching the at least one hook and loop section on the first side of the sleeve to the at least one hook and loop section on the second side of the sleeve.

18. The method of claim 14, wherein the blood pressure cuff further comprises a ring at an end of the sleeve.

19. The method of claim 18, wherein the wrapping further comprises extending the blood pressure cuff through the ring.

* * * * *